(12) United States Patent
Getts et al.

(10) Patent No.: US 9,441,264 B2
(45) Date of Patent: *Sep. 13, 2016

(54) WHOLE TRANSCRIPTOME SEQUENCING

(71) Applicant: Genisphere, LLC, Hatfield, PA (US)

(72) Inventors: Robert C. Getts, Collegeville, PA (US); James Kadushin, Gilbertsville, PA (US)

(73) Assignee: Genisphere, LLC, Hatfield, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/074,958

(22) Filed: Nov. 8, 2013

(65) Prior Publication Data

US 2014/0113333 A1    Apr. 24, 2014

Related U.S. Application Data

(63) Continuation of application No. 13/025,585, filed on Feb. 11, 2011, now Pat. No. 8,617,817.

(60) Provisional application No. 61/304,066, filed on Feb. 12, 2010.

(51) Int. Cl.
  *C12Q 1/68*    (2006.01)
  *C12N 15/10*    (2006.01)

(52) U.S. Cl.
  CPC .......... *C12Q 1/6806* (2013.01); *C12N 15/1096* (2013.01)

(58) Field of Classification Search
  None
  See application file for complete search history.

(56) References Cited

U.S. PATENT DOCUMENTS

| | | | |
|---|---|---|---|
| 7,550,264 B2 * | 6/2009 | Getts et al. | 435/6.12 |
| 2006/0281153 A1 | 12/2006 | Getts et al. | |
| 2008/0160581 A1 | 7/2008 | Getts et al. | |
| 2009/0227009 A1 * | 9/2009 | Sooknanan | 435/320.1 |

FOREIGN PATENT DOCUMENTS

| WO | WO-2007/035742 | 3/2007 |
|---|---|---|
| WO | WO-2009/117698 | 9/2009 |

OTHER PUBLICATIONS

Holt et al. (The new paradigm of flow cell sequencing, Genome Res. Jun. 2008;18(6):839-46).*

Mamanova et al., FRT-seq: amplification-free, strand-specific transcriptome sequencing, Nat Methods. Feb. 2010;7(2):130-2. doi: 10.1038/nmeth.1417. Epub Jan 17, 2010.*

"Applied Biosystems SOLiD 4 System, Library Preparation Guide", *Applied Biosystems* Apr. 2010, 259 pgs.

"mRNA Sequencing—Sample Preparation Guide", *illumina* Sep. 2009, 24 pgs.

PCT International Search Report & Written Opinion in PCT/US2011/024559, mailed May 20, 2011, 11 pgs.

"Preparation of SOLiD System Fragment Libraries for Targeted Resequencing using NibleGen Microarrays or Solution Phase Sequence Capture", *Human Genome Sequencing Center*, Baylor College of Medicine Aug. 30, 2010, 9 pgs.

Armour, Christopher D. et al., "Digital transcriptome profiling using selective hexamer priming for cDNA synthesis", *Nature Methods*, vol. 6, No. 9 Sep. 2009, 4 pgs.

Holt, Robert A. et al., "The new paradigm of flow cell sequencing", *Genome Research*, 18 2008, 839-846.

Kozarewa, Iwanka et al., "Amplification-free Illumina sequencing-library preparation facilitates improved mapping and assembly of (G+C)-biased genomes", *Nature Methods*, vol. 6, No. 4 Apr. 2009, 291-295.

Mamanova, Lira et al., "FRT-seq: amplification-free, strand-specific transcriptome sequencing", *Nature Methods*, 29 pgs.

Metzker, Michael L., "Sequencing technologies—the next generation", *Nature Reviews/Genetics*, vol. 11 Jan. 2010, 16 pgs.

Cheung, Foo et al., "Sequencing Medicago truncatula expressed sequenced tages using 454 Life Sciences technology", *BMC Genomics* Oct. 24, 2006, 10 pgs.

* cited by examiner

*Primary Examiner* — Aaron Priest
(74) *Attorney, Agent, or Firm* — Servilla Whitney LLC

(57) ABSTRACT

Methods for preparing strand-specific sequencing libraries of oligonucleotides using an RNA polymerase promoter to re-transcribe antisense cDNA which has been reverse transcribed from mRNA are provided. The transcription step linearly amplifies sRNA prior to production of double-stranded cDNA to be sequenced and may be sufficient to eliminate the conventional PCR amplification step prior to sequencing. The methods incorporate anchor sequences, amplification sequences and other sequences required for a particular sequencing system or reaction by hybridization and extension of primers, and transcription of RNA, rather than ligation, thus reducing the number of steps and the time required for sample preparation for sequencing of RNA. Use of primer hybridization and transcription reactions in the methods also results in a library that exhibits reduced 3' sequence bias.

19 Claims, 6 Drawing Sheets

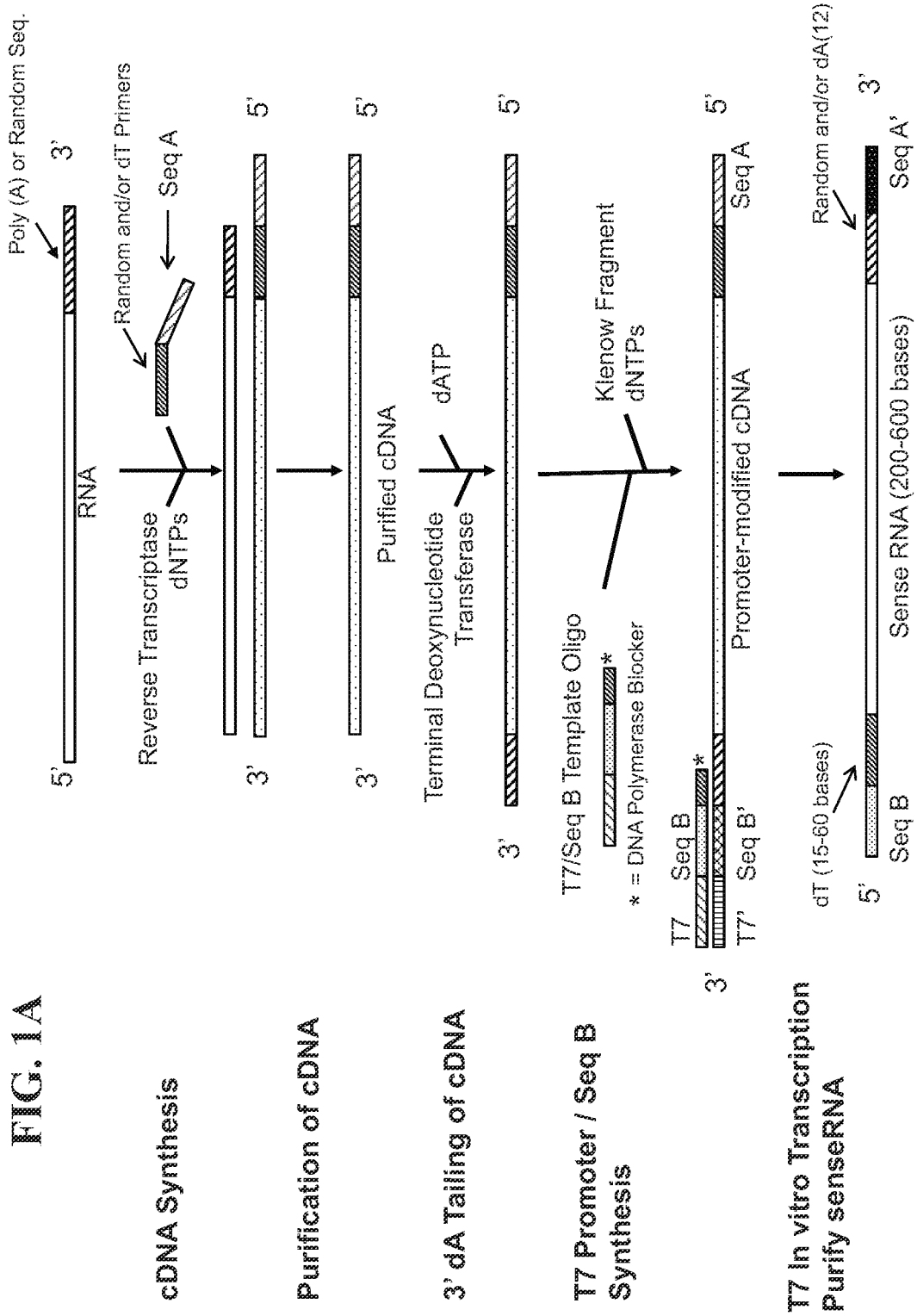

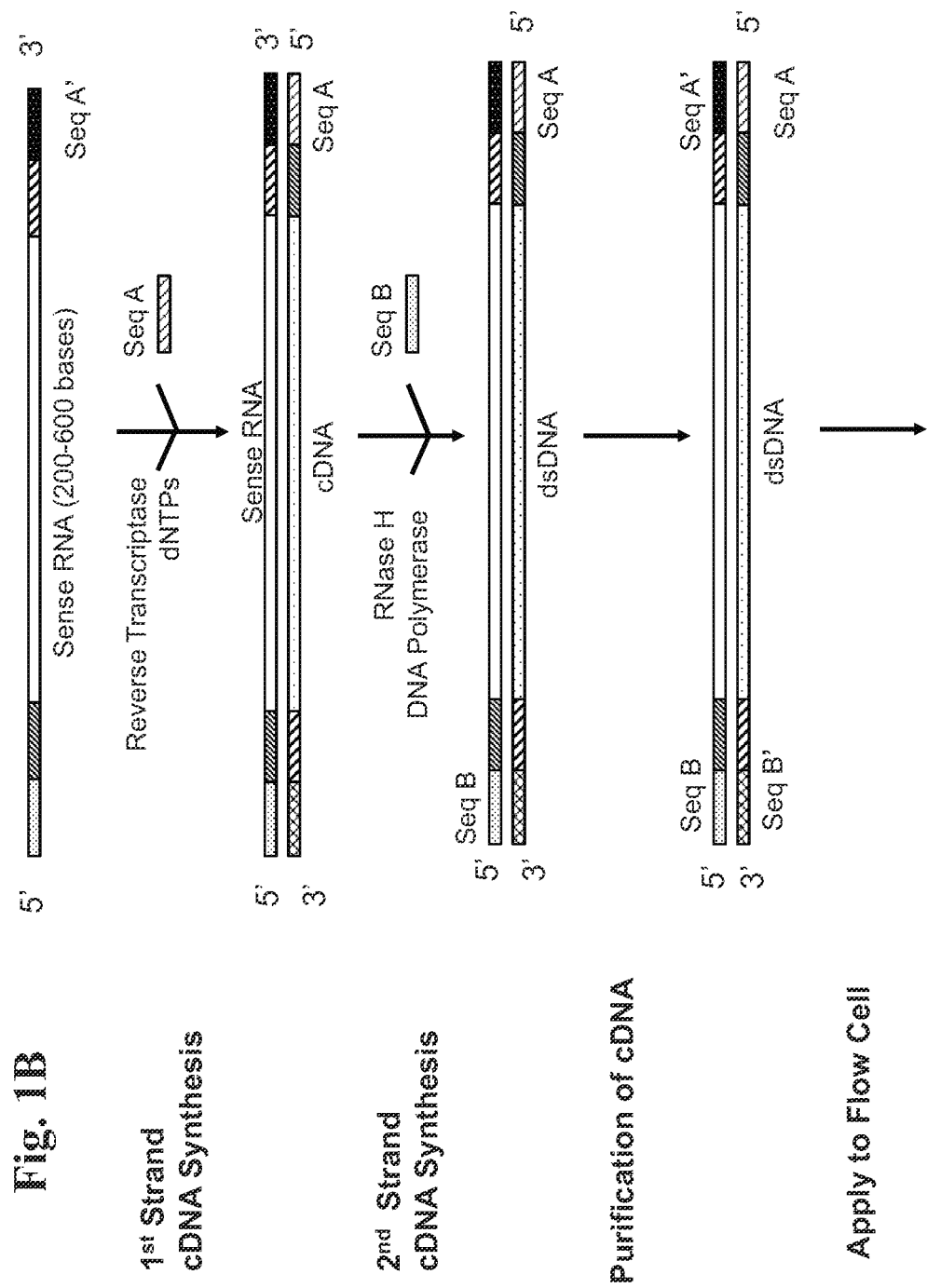

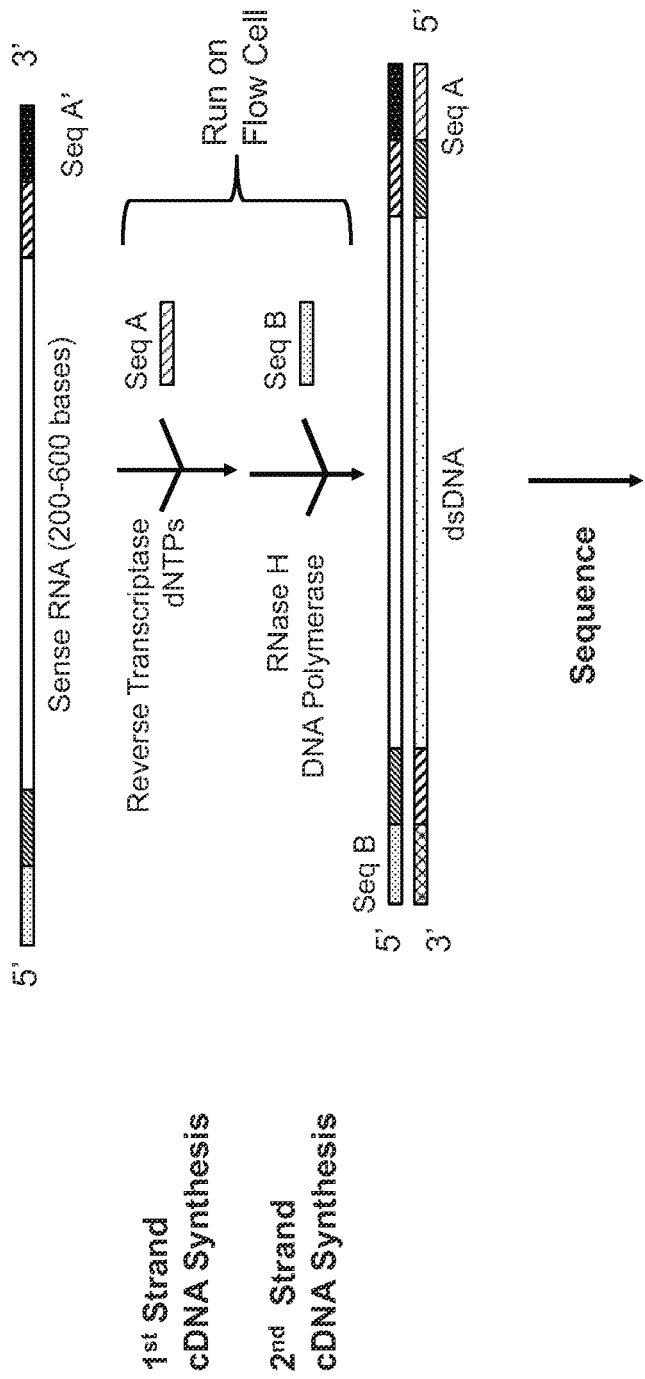

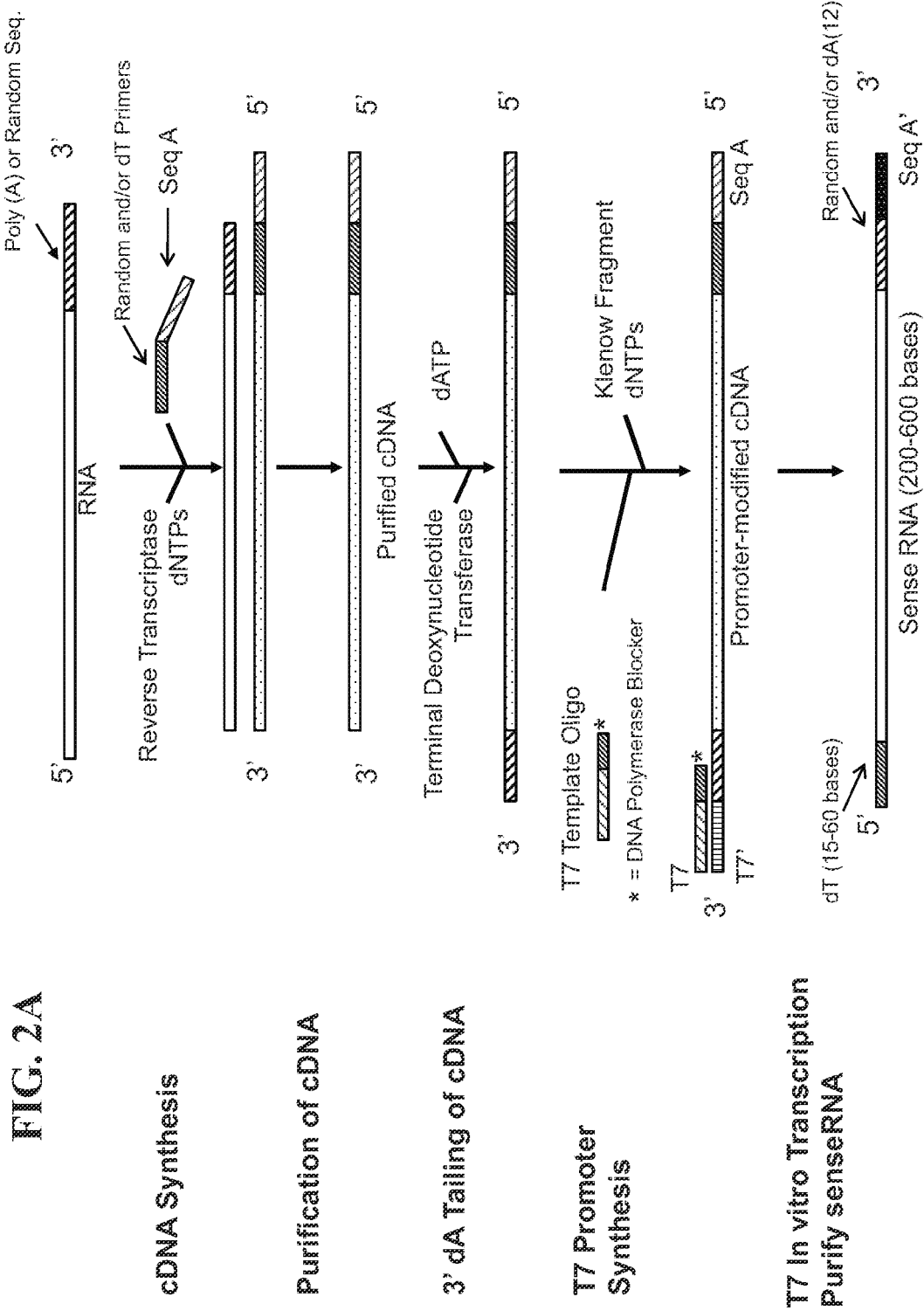

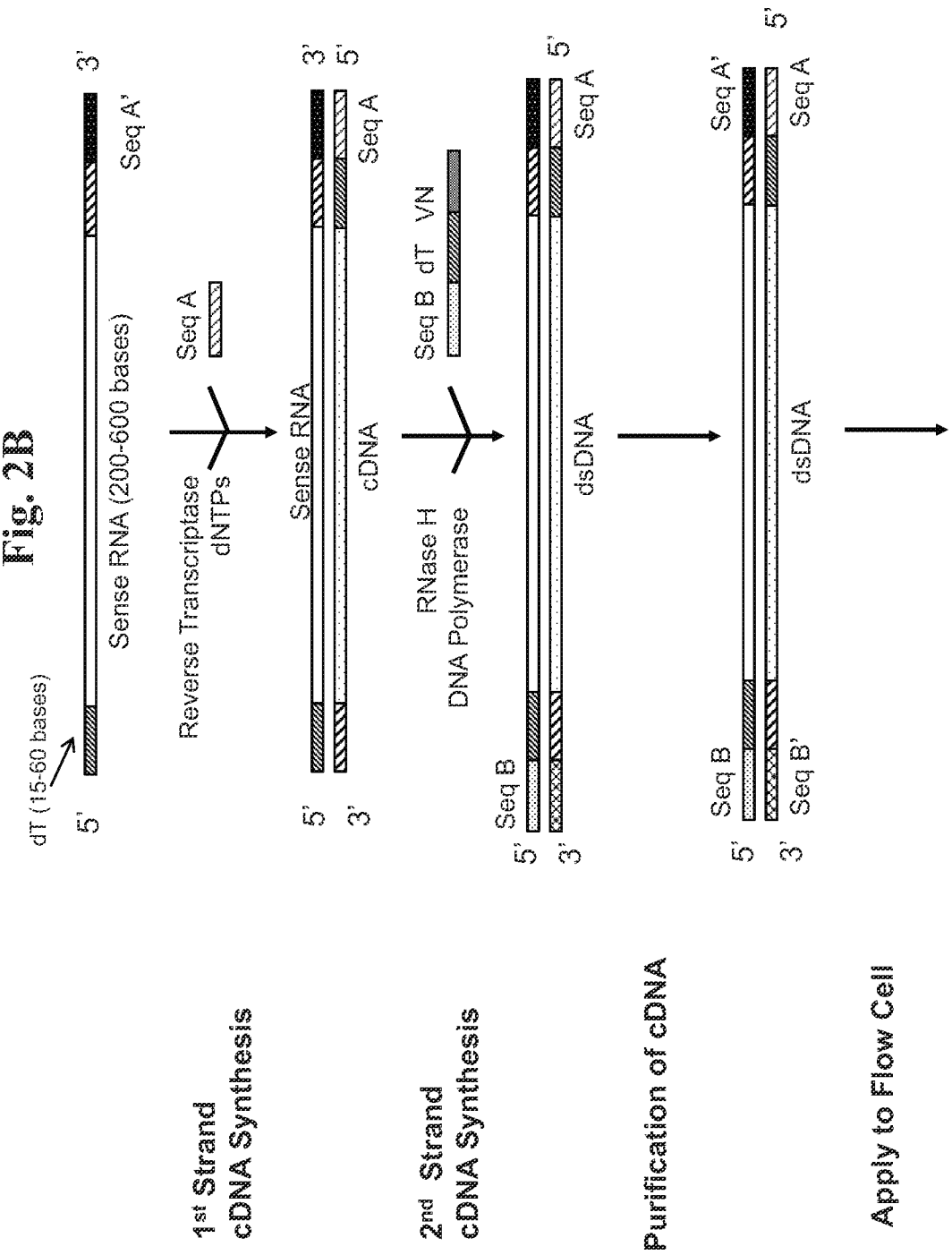

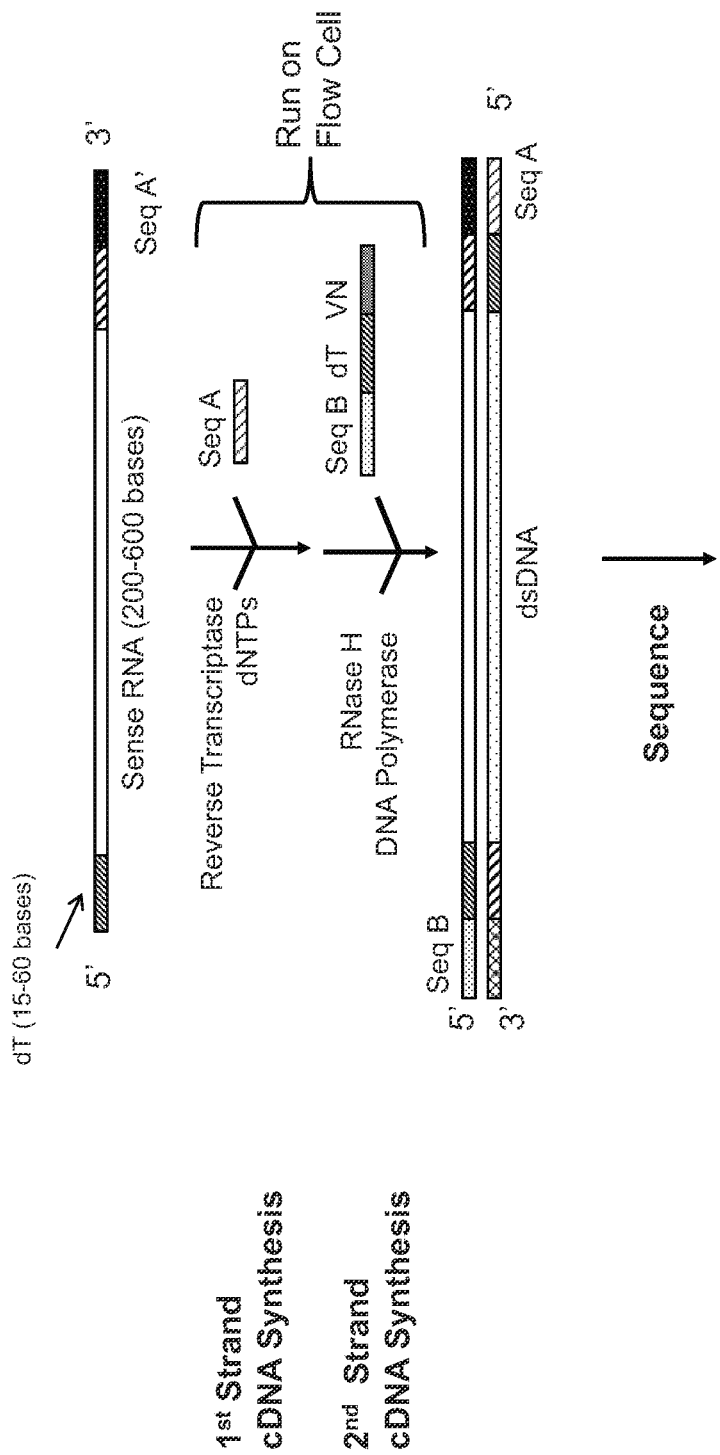

WHOLE TRANSCRIPTOME SEQUENCING

CROSS-REFERENCE TO RELATED APPLICATIONS

This application is a continuation of pending U.S. application Ser. No. 13/025,585, filed Feb. 11, 2011, which claims the benefit of U.S. Provisional Application Ser. No. 61/304,066, filed Feb. 12, 2010.

TECHNICAL FIELD

The invention relates to materials and methods for preparation of double-stranded DNA for sequencing of mRNA.

REFERENCE TO SEQUENCE LISTING

The material contained in the text file identified as "DSC0040-00US Sequence Listing_ST25.txt" (created Feb. 10, 2011; 2,011 bytes) is hereby incorporated by reference.

BACKGROUND

Current procedures for preparation of samples for sequencing of total cellular RNA require converting the total RNA into a DNA library of molecules suitable for high throughput DNA sequencing. Purified RNA or RNA fragments are reverse transcribed into first strand cDNA using poly(dT) or random primers. This is followed by second strand cDNA synthesis in the presence of RNaseH and DNA polymerase I. The template is typically amplified prior to sequencing, for example using PCR, to obtain sufficient amounts of material for the sequencing reaction. Amplification may be performed prior to attachment of the DNA to a solid surface as in the Roche/454 system (Hoffman LaRoche). In some systems solid-phase amplification is used to produce randomly distributed, clonally amplified clusters of templates on a glass slide, with forward and reverse primers also covalently attached to the slide (Illumina/Solexa). Current sequencing methods are therefore capable of providing thousands of prepared template molecules immobilized on a solid surface or support, resulting in spatially separated template sites which allow thousands of sequencing reactions to be performed simultaneously.

Because of the requirements for amplification of the template and attachment to solid surfaces, the isolated RNA must be modified during sample preparation by appending sequences for use in amplification (e.g., PCR primer sites) and attachment (e.g., adapters specific for the sequencing system or reaction being used). These are typically cumbersome, multi-step processes that can take up to two days to complete. For example, the Illumina mRNA sample preparation procedure involves several steps to prepare the double-stranded cDNA for sequencing, all of which are performed prior to application to the solid support: end-repair, addition of an "A" base to the 3' ends, ligation of adapters, purification of the ligation product and PCR amplification. The entire protocol requires two days to complete.

It is desirable in genome and transcriptome sequencing to be able to identify which strand of the double strand cDNA is being sequenced. Although the available sequencing systems typically append different adapter sequences to each end of the molecule during sample preparation, this does not produce a strand-specific or oriented library which would allow identification of the strand being sequenced.

There therefore exists a need for methods of preparing whole mRNA for sequencing that produce strand-specific libraries adaptable to a variety of sequencing instruments and systems and that reduce the time required for sample preparation. The present invention meets these needs.

SUMMARY

One aspect of the invention provides methods for preparing strand-specific sequencing libraries of oligonucleotides using an RNA polymerase promoter to re-transcribe reverse-transcribed cDNA to produce sense RNA. As this transcription step also linearly amplifies the RNA to be sequenced (referred to herein as "preamplification"), it may be sufficient to eliminate the conventional PCR amplification step prior to sequencing.

Another aspect of the invention provides methods for incorporation of anchor sequences, amplification sequences and other sequences required for a particular sequencing system or reaction by hybridization and extension of primers, and transcription of RNA rather than ligation, thus further reducing the number of steps and the time required for sample preparation for sequencing of RNA. By incorporating the promoter and transcribing from the 3' end of the antisense cDNA, these methods also result in a library with reduced 3' bias in the sRNA population subsequently used to construct the double-stranded cDNA library used for sequencing.

In yet another aspect, the sense RNA produced by the preamplification step of the invention may be applied directly to the sequencing chip and the remaining steps for production of double-stranded DNA (dsDNA) for sequencing may be performed on the chip.

In a specific exemplary embodiment, the invention provides methods for producing double stranded cDNA from mRNA for use in a sequencing reaction, the methods comprising:

a) reverse transcribing an isolated mRNA using a first primer hybridized thereto, the first primer comprising a random sequence or poly(dT) at a 3' end thereof and a first sequence required for a selected sequencing reaction at a 5' end thereof, thereby producing a first cDNA comprising the first sequence required for the selected sequencing reaction at a 5' end thereof;

b) adding a first 3' homopolymeric tail to the first cDNA;

c) hybridizing a single-stranded oligonucleotide to the 3' homopolymeric tail of the first strand cDNA, the single-stranded oligonucleotide comprising a 5' RNA polymerase promoter sequence and a second 3' homopolymeric tail which is complementary to the first 3' homopolymeric tail, thereby producing a partially double-stranded DNA with a 5' single-stranded overhang comprising the RNA polymerase promoter sequence;

d) extending the 3' end of the cDNA, thereby producing a double stranded RNA polymerase promoter e) transcribing sRNA from the double-stranded RNA polymerase promoter, the sRNA comprising a complement of the first sequence required for the selected sequencing reaction at a 3' end thereof;

f) reverse transcribing the sRNA using a second primer comprising the first sequence required for the selected sequencing reaction at a 3' end thereof, thereby producing a second cDNA comprising the first sequence required for the selected sequencing reaction at a 5' end thereof; and g) hybridizing to the second cDNA a third primer comprising a second sequence required for the selected sequencing reaction at a 3' end thereof and extending the third primer, thereby producing the double-stranded cDNA for use in the sequencing reaction.

In other embodiments of the invention, the single-stranded oligonucleotide may further comprise the second sequence required for the selected sequencing reaction between the RNA polymerase promoter and the 3' poly(dT) tail.

BRIEF DESCRIPTION OF THE DRAWINGS

FIG. 1A-C illustrates one embodiment of the dsDNA preparation methods of the invention.

FIG. 2A-C illustrates a second embodiment of the dsDNA preparation methods of the invention.

DETAILED DESCRIPTION

Before describing several exemplary embodiments of the invention, it is to be understood that the invention is not limited to the details of construction or process steps set forth in the following description. The invention is capable of other embodiments and of being practiced or being carried out in various ways.

Basic techniques in the field of molecular biology relevant to the procedures described herein are described, for example, in Sambrook, et al., *Molecular Cloning, A Laboratory Manual* (3d ed. 2001) and Ausubel, et al., *Current Protocols in Molecular Biology* (1994).

One embodiment of the invention provides methods for preparing double-stranded cDNA for sequencing, wherein a sequence required for a selected sequencing system or reaction is appended to isolated mRNA by hybridization and extension of a single-stranded DNA primer comprising the required sequence at its 5' end (reverse transcription). The cDNA thus produced is tailed with a homopolymeric tail at the 3' end and hybridized to a single-stranded oligonucleotide comprising a 5' RNA polymerase promoter and a 3' homopolymeric tail complementary to the 3' homopolymeric tail of the cDNA. The recessed 3' end of the cDNA hybridized to the RNA polymerase promoter oligonucleotide is filled in and rendered double-stranded, activating the RNA polymerase promoter and enabling transcription of sRNA from the antisense cDNA template. The sRNA is again reverse transcribed by hybridization and extension of a primer comprising the sequence required for the selected sequencing system or reaction at its 3' end. Second strand cDNA synthesis on this cDNA template produces the desired double-stranded cDNA with the sequence required for the selected sequencing system or reaction appended at one end. The double-stranded cDNA can then be sequenced in the selected sequencing system or reaction.

Optionally, the 3' terminus of the single-stranded oligonucleotide comprising the RNA polymerase promoter may be blocked to prevent extension of the oligonucleotide by DNA polymerase. The blocked 3' terminus is not necessary for transcription of the cDNA template to produce the sRNA. However, in general it has been observed that blocking extension of the 3' end results in more efficient transcription of sRNA compared to an RNA polymerase promoter oligonucleotide which is extendable.

The embodiment described above may be adapted to append sequences required for the selected sequencing system or reaction at both ends of the double-stranded cDNA. In this embodiment the cDNA produced by reverse transcription of the mRNA and tailed with a homopolymeric tail at the 3' end is hybridized to a single-stranded oligonucleotide comprising the 5' RNA polymerase promoter, a 3' homopolymeric tail which is complementary to the 3' homopolymeric tail of the cDNA, and further comprising a second sequence required for the selected sequencing system or reaction between the promoter and the 3' homopolymeric tail of the single-stranded oligonucleotide. When the recessed 3' end of the cDNA hybridized to the RNA polymerase promoter oligonucleotide is filled in and rendered double-stranded to activate the RNA polymerase promoter, the transcribed sRNA comprises the second sequence required for the selected sequencing system or reaction at the 5' end. Reverse transcription of the sRNA by hybridization and extension of a primer comprising the first sequence required for the selected sequencing system or reaction followed by second strand cDNA synthesis using a primer comprising the second sequence required for the selected sequencing system or reaction produces the desired double-stranded cDNA with a sequence required for the selected sequencing system or reaction appended at each end. The double-stranded cDNA can then be sequenced in the selected sequencing system or reaction. In this embodiment the 3' terminus of the single-stranded oligonucleotide comprising the RNA polymerase promoter may optionally be blocked to prevent extension of the oligonucleotide by DNA polymerase, as discussed above.

The embodiments described above may be further adapted to append additional sequences required for a selected sequencing system or reaction at either one or both ends of the double-stranded cDNA. For example, if the selected sequencing system or reaction requires anchor sequences, sequencing primer hybridization sequences and amplification primer hybridization sequences appended to the double-stranded cDNA, the primers of either embodiment described above may be modified by incorporation of the additional sequences into the primers. Additional sequences required for the selected sequencing system or reaction may be included at the 5' end of the primer used for reverse transcription of the sRNA and/or at the 5' end of the primer used for second strand cDNA synthesis in the last step of the process.

A first specific embodiment of the invention is shown in FIG. 1 A-C. Turning to FIG. 1A, total isolated mRNA is hybridized to single-stranded DNA primers comprising a random sequence or poly-dT at their 3' ends and a 5' sequence corresponding to a sequence (SeqA) required for a selected sequencing system or reaction (e.g., the anchor sequence for capturing the cDNA on a sequencing chip). The hybridized primers are then extended on the mRNA template using reverse transcriptase and dNTPs to produce a double-stranded RNA-DNA molecule with SeqA at the 5' end of the cDNA strand. The cDNA is then purified, for example using RNeasy or Agencourt Beads, and a 3' dA tail is added using terminal deoxynucleotide transferase and dATP. A single-stranded transcription oligonucleotide is then hybridized to the modified 3' end of the cDNA. The transcription oligonucleotide (T7/SeqB Template Oligo) comprises a 5' RNA polymerase promoter sequence (e.g., a T7 promoter), an interior sequence corresponding to a second sequence (SeqB) required for the selected sequencing system or reaction (e.g, the second anchor or adapter sequence for capturing the cDNA on the sequencing chip), a 3' dT tail, and a DNA polymerase blocker at the 3' end. Addition of DNA polymerase (Klenow fragment) and dNTPs results in extension of the recessed 3' end of the cDNA, producing an active double-stranded RNA polymerase promoter without synthesis of second strand cDNA. The RNA polymerase promoter is thus appended to the 5' end of the reverse transcribed cDNA. The double-stranded RNA polymerase promoter is then used to drive transcription of the first strand cDNA template by addition of an RNA polymerase which recognizes the selected promoter. The sense RNA (sRNA) resulting from this preamplification transcription reaction reproduces the original mRNA sequence with the two sequences required for the selected sequencing system or reaction appended at each end (SeqA' and Seq B). By appending the RNA polymerase promoter to the 5' end of the first strand cDNA the method of the invention reduces the 3' sequence bias often associated with conventional RNA amplification methods.

As shown in FIG. 1B, the sRNA may then be subjected to reverse transcription using a single-stranded antisense primer comprising SeqA at the 3' end and additional sequences required for the selected sequencing system or reaction at the 5' end (e.g., the PCR amplification site and/or sequencing primer site—5' additional sequences of antisense primer comprising Seq A not shown in FIG. 1B and FIG. 1C). The antisense primer is hybridized to the sRNA and extended using reverse transcriptase and dNTPs to produce a double-stranded sRNA/cDNA hybrid comprising the complete set of sequences required for the sequencing library at each end. The sRNA strand is then degraded (for example using an RNase such as RNase H or NaOH) and a second strand sense primer comprising SeqB at the 3' end and second additional sequences required for the selected sequencing system or reaction at the 5' end (e.g., the second PCR amplification site and/or sequencing primer site—5' additional sequences of the second strand sense primer comprising SeqB not shown in FIG. 1B and FIG. 1C) is hybridized to the antisense cDNA strand. The second strand sense primer is extended with DNA polymerase and dNTPs to produce a dsDNA molecule with all of the sequences required for the selected sequencing system or reaction at both ends. After purification, the dsDNA is applied to the flow cell and sequenced according to the methods of the selected sequencing system or reaction.

Alternatively, as shown in FIG. 1C, the sRNA produced in FIG. 1A may be applied directly to the flow cell for production of dsDNA for sequencing. In this embodiment hybridization and extension of the antisense primer, degradation of sRNA in the sRNA/cDNA hybrid and hybridization and extension of the sense primer described above occur on the flow cell. Methods for use in the invention for capture of oligonucleotides on the flow cell, reverse transcription and sequencing are described by Mamanova, et. al *Nature Methods,* 7(2):130-132 (2010).

A second specific embodiment of the invention is shown in FIG. 2A-C. Turning to FIG. 2A, total isolated mRNA is hybridized to single-stranded primers comprising random sequences or poly-dT at their 3' ends and a 5' sequence corresponding to a sequence (SeqA) required for a selected sequencing system or reaction (e.g., the anchor or adapter sequence for capturing the cDNA on a sequencing chip). The hybridized primers are extended on the mRNA template using reverse transcriptase and dNTPs to produce a double-stranded RNA-DNA molecule with SeqA at the 5' end of the cDNA strand. The cDNA is then purified, for example using RNeasy or Agencourt Beads, and a 3' dA tail is added using terminal deoxynucleotide transferase and dATP. A single-stranded transcription oligonucleotide is then hybridized to the modified 3' end of the cDNA. The transcription oligonucleotide comprises a 5' RNA polymerase promoter sequence (e.g., a T7 promoter), a 3' dT tail, and a DNA polymerase blocker at the 3' end. Addition of DNA polymerase (Klenow fragment) and dNTPs results in extension of the recessed 3' end of the cDNA, producing an active double stranded RNA polymerase promoter which is then used to drive transcription of the cDNA template by addition of an RNA polymerase which recognizes the selected promoter. The sense RNA (sRNA) resulting from this preamplification transcription reaction reproduces the original mRNA sequence with poly dT appended to the 5' end and a sequence required for the selected sequencing system or reaction appended to the 3' end (SeqA').

As shown in FIG. 2B, the sRNA may then be subjected to reverse transcription using a single-stranded antisense primer comprising SeqA at the 3' end and additional sequences required for the selected sequencing system or reaction at the 5' end (e.g., the PCR amplification site and/or sequencing primer site—5' additional sequences of antisense primer comprising Seq A not shown in FIG. 2B and FIG. 2C). The antisense primer is hybridized to the sRNA and extended using reverse transcriptase and dNTPs to produce a double-stranded sRNA/cDNA hybrid comprising the complete set of sequences required for the sequencing library at one end and poly dT at the other end. The sRNA strand is then degraded using RNase H and a second strand sense primer comprising SeqB at the 5' end, interior second additional sequences required for the selected sequencing system or reaction (e.g., the second PCR amplification site and/or sequencing primer site—5' additional sequences of second strand sense primer comprising Seq B not shown in FIG. 2B and FIG. 2C) and a poly dT sequence at the 3' end is hybridized to the antisense cDNA strand. The second strand sense primer may optionally include a V nucleotide (i.e., any nucleotide except T or U) or a VN sequence (i.e., any nucleotide except T or U followed by any nucleotide) at its most 3' end to ensure that the primer hybridizes at, and is anchored to, the antisense cDNA at the junction of the poly dA segment and the cDNA sequence. The sense primer is extended with DNA polymerase and dNTPs which fills in the 5' overhang of SeqB and the additional sequences required for the selected sequencing system or reaction and synthesizes a sense cDNA sequence, thereby producing a dsDNA molecule with all of the sequences required for the selected sequencing system or reaction at both ends. After purification, the dsDNA is applied to the flow cell and sequenced according to the methods of the selected sequencing system or reaction.

Alternatively, as shown in FIG. 2C, the sRNA produced in FIG. 2A may be applied directly to the flow cell for production of dsDNA for sequencing. In this embodiment hybridization and extension of the antisense primer, degradation of sRNA in the sRNA/cDNA hybrid and hybridization and extension of the sense primer described above occur on the flow cell. Methods for use in the invention for capture of oligonucleotides on the flow cell, reverse transcription and sequencing are as described by Mamanova, et. al *Nature Methods,* 7(2):130-132 (2010).

The foregoing methods for preparation of total mRNA for sequencing are exemplified using a T7 RNA polymerase promoter for preamplification and generation of sRNA. However, any promoter recognized by RNA polymerase for transcription of RNA on a DNA template may be used in the methods of the invention, for example promoters recognized by bacteriophage RNA polymerase such as T7, T3 or SP6 RNA polymerase promoters.

In any of the foregoing methods, if a DNA polymerase blocker is present at the 3' end of the transcription oligonucleotide (i.e., the single-stranded oligonucleotide comprising the RNA polymerase promoter) it may be a 3' amino modifier, a 3' deoxyterminator, a 3' dideoxyterminator or any other modification that prevents extension of the 3' end by DNA polymerase.

In any of the foregoing methods, the homopolymeric tail appended to the cDNA after reverse transcription of the mRNA may be any homopolymeric string of nucleotides (e.g., A, C, T or G). However, in a specific example, the 3' homopolymeric tail of the cDNA is poly(dT or poly(dA). In addition, the selection of the 3' homopolymer to be appended to the cDNA produced by reverse transcription of the mRNA determines the nucleotides of the 3' homopolymeric tail of the single-stranded oligonucleotide comprising the RNA polymerase promoter. Specifically, any homopolymeric string of nucleotides which is complementary to the 3' homopolymeric tail of the cDNA is useful as the 3' homopolymeric tail of the single-stranded oligonucleotide. In a specific example, however, if the 3' homopolymeric tail of the cDNA is poly(dA) the complementary 3' homopolymeric tail of the single-stranded oligonucleotide will be poly(dT) and if the 3' homopolymeric tail of the cDNA is poly(dT) the complementary 3' homopolymeric tail of the single-stranded oligonucleotide will be poly(dA).

In any of the foregoing methods, any primer with a 3' homopolymeric sequence which hybridizes to a 3' homopolymeric sequence or tail of an oligonucleotide may optionally terminate at its 3' end with the nucleotide sequence AB-3' (if the homopolymeric sequence or tail of the oligonucleotide is poly(dT), wherein B is any nucleotide other than A); with the nucleotide sequence CD-3' (if the homopolymeric sequence or tail of the oligonucleotide is poly(dG), wherein D is any nucleotide other than C); with GH-3' (if the homopolymeric sequence or tail of the oligonucleotide is poly(dC), wherein H is any nucleotide other than G); or with the nucleotide sequence TV-3' (if the homopolymeric sequence or tail of the oligonucleotide is poly(dA), wherein V is any base other than T or U). This ensures that the primer hybridizes to the oligonucleotide at the junction of the homopolymeric sequence or tail and the 3' terminal nucleotide of the sense or antisense sequence of the oligonucleotide, thus anchoring the 3' end of the primer to the oligonucleotide template. Alternatively, such primers may optionally terminate with ABN-3', CDN-3', GHN-3' or TVN-3' to provide a two-nucleotide anchor when the primer is hybridized at the junction of the homopolymeric sequence or tail of the oligonucleotide and the 3' terminal nucleotide of the sense or antisense sequence of the oligonucleotide.

In any of the foregoing methods total mRNA to be prepared for sequencing may be isolated by any suitable method as is known in the art. For example, mRNA may be isolated on a solid phase using beads modified with oligo (dT) or using the RNAqueous® kit (Ambion). The isolated mRNA may be fragmented prior to preparation according to the methods described above (for example by heating), but fragmentation is not necessary. If a fragmented RNA sample is reverse transcribed according to the present invention it is generally desirable to use random sequence RT primers to generate first strand cDNA. The RNA may be obtained from any tissue or cellular source, including viral, prokaryotic and eukaryotic sources obtained from biological and environmental samples. In a specific embodiment, clinical samples such as FFPE samples ("formalin fixed and paraffin embedded") may be the source of total mRNA for use in the methods of the invention. In addition, any of the primers used in the foregoing methods may be obtained commercially or synthesized using procedures known in the art.

Any of the foregoing embodiments of the invention may also be modified to incorporate a two-round amplification process based on methods derived from U.S. Pat. No. 7,550,264, by adding a second RNA polymerase promoter sequence between the first RNA polymerase promoter (exemplified in the drawings as a T7 promoter) and Seq B defining nucleotides in the "promoter template". For example, a T3 promoter sequence can be added. Hybridization of the dual-promoter oligonucleotide to the poly(dA) tailed cDNA and filling in of the 3' recessed end of the cDNA thus results in two active RNA polymerase promoters available for the transcription step. In the first transcription reaction (i.e., the first linear amplification reaction) an RNA polymerase that recognizes the first (upstream) promoter is used to produce sRNA with the second (downstream) promoter at the 5' end. Reverse transcription of this molecule results in a cDNA which can be hybridized to a second 3'-blocked oligonucleotide via the second promoter sequence. After filling the recessed 3' end of the cDNA a second transcription reaction (i.e., the second linear amplification reaction) can be initiated using an RNA polymerase that recognizes the second promoter. Processing of the total sRNA produced from both amplification reactions can then continue as described above to produce double-stranded cDNA for sequencing.

In any of the foregoing embodiments, the primers, single-stranded oligonucleotides and optionally other reagents for performing transcription and/or primer extension reactions may be packaged in the form of a kit for producing double-stranded cDNA from mRNA for use in a DNA sequencing system or reaction. As an example, such a kit may comprise first primer comprising a random nucleotide sequence or poly(dT) at a 3' end thereof and a first sequence required for a selected sequencing reaction at a 5' end thereof; a single-stranded oligonucleotide comprising a 5' RNA polymerase promoter sequence and a 3' homopolymeric tail; a second primer comprising the first sequence required for the selected sequencing reaction at a 3' end thereof; a third primer comprising a second sequence required for the selected sequencing reaction at a 3' end thereof; and, optionally, one or more reagents for use in a reverse transcription reaction, a transcription reaction and/or a primer extension reaction. Optionally, the kit may further comprise instructions for producing double-stranded DNA from mRNA for use in the sequencing reaction. As discussed in certain embodiments, the single-stranded oligonucleotide may further comprises the second sequence required for the selected sequencing reaction between the RNA polymerase promoter and the 3' homopolymeric tail. The second primer may also further comprise at least a third sequence required for the selected sequencing reaction at a 5' end thereof. The third primer may also further comprise at least a fourth sequence required for the selected sequencing reaction at a 5' end thereof. If instructions for performing the reactions using the primers and single-stranded oligonucleotides to produce double-stranded cDNA for DNA sequencing are included in the kit, such instructions may include instructions for performing the reactions on a flow cell for DNA sequencing.

Because the inventive methods rely on transcription and primer extension reactions to produce the double-stranded cDNA, the final product includes homopolymeric sequences internal and adjacent to the appended sequences required for the selected sequencing system or reaction (see the FIG. 1B and FIG. 2B cDNA constructs immediately preceding "Apply to Flow Cell"). These homopolymeric sequences are derived from the primers and the RNA polymerase promoter oligonucleotide. Long homopolymeric regions such as poly (dA) or poly(dT) typically cause DNA sequencing errors and "noise" through the homopolymer region and downstream of it, possibly because the homopolymer region is not properly paired during polymerization (sometimes referred to as "slippage"). Although accurate sequence data can often be obtained by sequencing in the opposite direction, this solution is cumbersome and may not be reliable in every instance.

The foregoing embodiments may further include materials and methods for resolving potential sequencing errors and sequence slippage problems which could result from the homopolymeric regions of the cDNA which are downstream of sequencing primers used in the selected sequencing system or reaction because the location, sequence and length of the homopolymeric region are known. Modification of the sequencing primer to provide a 3' homopolymeric tail which is complementary to the homopolymeric segment of the cDNA to be sequenced allows sequencing to begin downstream of the homopolymeric sequence in the cDNA and avoids potential sequencing errors in this region. In a particular embodiment, the complementary 3' homopolymeric tail of the sequencing primer is also of similar length to the homopolymeric sequence in the cDNA. The appropriate 3' homopolymeric tail can be added to any sequencing primer known in the art, including the sequencing primers used by commercial sequencing systems such as Illumina/Solara Genome Analyzer, the Roche 454 system and the ABI SOLiD. These 3'-homopolymeric tailed sequencing primers may be included in the kits of the invention, or the sequencing primer(s) used by a particular commercial sequencing system may be included in the kit with instructions and/or reagents for tailing the sequencing primer by the end-user.

An alternative method for resolving potential sequencing errors and sequence slippage problems which could result from the homopolymeric regions of the cDNA in the foregoing embodiments of the invention employs running multiple cycles of "dark sequencing" to sequence through the homopolymer region. "Dark sequencing" is a method known in the art in which the sequencing reaction is performed with nucleotides which are not fluorescently labeled. The number of sequencing cycles that are performed without fluorescent label generally is selected to correspond to the length of the homopolymeric region, after which the sequencing reaction is continued in the usual manner in the presence of fluorescently labeled nucleotides. Dark sequencing may require 1 to 50 sequencing cycles to resolve the homopolymeric region. In the various embodiments of the present invention, sequencing primers used by commercial sequencing systems as described above can be employed in dark sequencing reactions in the conventional manner to sequence the homopolymeric segments of the dsDNA produced by the inventive methods.

The embodiments of the invention described above pre-amplify the RNA to be sequenced, and therefore addition of the amplification primer recognition sequences typically required for solid phase sequencing systems or reactions is optional and may not be required in all cases. If the amplification primer recognition sequence is to be omitted from the final double stranded cDNA being sequenced, the antisense RT primer is modified accordingly. For example, the antisense RT primer sequence may comprise only the anchor sequence and the sequencing primer recognition site used in the selected sequencing system or reaction. Similarly, the second strand sense primer sequence may comprise only the second anchor sequence and the second sequence primer recognition site.

Preamplification of the oligonucleotide to be sequenced is a linear amplification process accomplished by transcription of the target sequence from the appended RNA polymerase promoter. This process substantially shortens the time required to prepare RNA for DNA sequencing. The transcription reaction can produce sufficient oligonucleotide for construction of the cDNA library in as little as 15 min., for example from 15 min. to overnight or from 15 min. to 1 hr. If additional amplification is desired, the transcription reaction may be allowed to proceed overnight. The linear preamplification feature of the invention allows construction of a cDNA library representing the total transcriptome to be prepared in one day or in as little as a half day.

The RNA preamplification feature of the invention also eliminates the need to repeatedly quantify the concentration of cDNA post-PCR amplification to determine the amount of the preparation to put on the chip. This is because transcription amplification is linear rather than exponential, so the amount of transcript produced can be accurately calculated based on the length of time the transcription reaction is allowed to run. This is not the case for exponential amplification reactions such as PCR.

In the following Examples the anchor, sequencing and amplification sequences (collectively and individually referred to as adapter sequences) used in the methods of the invention are those associated with the Illumina Genome Analyzer sequencing system. However, these adapter sequences may be replaced in any of the foregoing methods with any of the adapter sequences required by a selected sequencing system or reaction to conform the primers to that particular system design. For example, the Applied Biosystems SOLiD™ System sequencing platform for DNA uses truncated-TA adapters for capture of the DNA on the microarray and pre-capture amplification by PCR. See Protocol Version 2.1, Baylor College of Medicine, Human Genome Sequencing Center, "Preparation of SOLiD™ System Fragment Libraries for Targeted Resequencing using NimbleGen Microarrays or Solution Phase Sequence Capture." In a further example, the Applied Biosystems SOLiD 4 System employs P1 and P2 adapters for sequencing and PCR primer recognition as set forth in the Library Preparation Guide (April 2010). Adapters which provide priming sequences for both amplification and sequencing of library fragments for use with the 454 Life Science GS20 sequencing system are described by F. Cheung, et al. *BMC Genomics* 2006, 7:272. These and other sequences required for a selected sequencing system or reaction can be incorporated into the primers and oligonucleotides of the invention as taught herein to provide cDNA libraries having the appropriate appended end-sequences for the selected sequencing system or reaction.

Representative web sources for information on sequencing adapters, capture sequences and primer recognition sequences are shown below: hgsc.bcm.tmc.edu/documents/Preparation_of_SOLiD_Capture_Libraries.pdf; biomedcentral.com/1471-2164/7/272/; and appliedbiosystems.com/cms/groups/mcb_support/documents/generaldocuments/cms_081746.pdf.

Example 1 sRNA Synthesis for Whole Transcriptome Sequencing

Method of FIG. 1A-C

1. First Strand cDNA Synthesis
   For each RNA sample, the following RNA/primer mix was prepared on ice:
   1. 1-8 µl total RNA (not exceeding 250 ng)
   2. 2 µl first round SeqA oligodT sequence specific RT primer (50 ng/µl) (5'-CTT CCG ATC TGA TTT TTT TTT TTV-3', where V=C, G or A deoxyribonucleotides; SEQ ID NO:1) or 1 µl first round SeqA random sequence specific RT primer (2× by mass of RNA) (5'-CTT CCG ATC TGA NNN NNN NNN-3, where N=A, G, C or T deoxyribonucleotides at random; SEQ ID NO:2)

3. RNase-free water to 11 µl

The first round RT primers (first strand RT primers) comprise a 5' extension 12 nucleotides long which corresponds to the anchor sequence used by the Illumina sequencing system and which also generates a specific nucleotide sequence binding site for the antisense first strand RT primers (see accompanying figures). The RNA/primer mixture was heated at 80° C. for 10 minutes and immediately cooled on ice for 1-2 min. The mixture was then mixed with 9 µl of a Master Mixture solution to bring the final volume to 20 µl containing 1×RT buffer (50 mM Tris-HCl (pH 8.3), 75 mM KCl, 3 mM $MgCl_2$), 10 mM dithiothreitol (DTT), 0.5 mM each dNTP, 10 U Superase-In™ (Ambion), and 200 U Superscript™ II reverse transcriptase (Invitrogen). The mixture was briefly centrifuged and incubated at 42° C. for 2 hrs. Following a brief centrifugation, the reaction was adjusted to 100 µl with 1×TE (10 mM Tris-HCl, pH 8.0, 1 mM EDTA).

2. cDNA Purification

The reaction was purified using the RNeasy MinElute™ Kit (Qiagen) according to the manufacturer's protocol and eluted in 10 µl Nuclease-Free water provided by the manufacturer.

3. Tailing of First Strand cDNA

The first strand cDNA molecules were heated at 80° C. for 10 minutes and immediately cooled on ice for 1-2 min. The cDNA molecules in 10 µl were then mixed with 10 µl of a Master Mixture solution to bring the final volume to 20 µl containing 1× Tailing buffer (10 mM Tris-HCl, pH 7.0, 10 mM $MgCl_2$), 2.0 mM dATP, and 10 U terminal deoxynucleotidyl transferase (Roche Diagnostics). The mixture was briefly centrifuged and incubated at 37° C. for 2 min. The reaction was stopped by heating at 80° C. for 10 min and cooled at room temperature for 1-2 minutes.

4. T7 Promoter Synthesis

One µl of T7/SeqB RNA polymerase promoter template oligonucleotide (5'-TAA TAC GAC TCA CTA TAG GGA CTT CCG ATC TCT TTT TTT TTT TT-3'; SEQ ID NO:3) (100 ng/µl) containing a 3' amino modifier was added to the oligodA-tailed cDNA molecules and the mixture incubated at 37° C. for 10 min to anneal the strands. The T7 RNA polymerase promoter template contains a T7 RNA polymerase promoter template (nucleotides 1-21) 5' to a universal sequence used as a binding site for DNA sequencing primers (nucleotides 22-32) and a 3' poly dT tail. The tailed cDNA molecules/promoter template mixture was then mixed with 3 µl of a Master Mixture solution to bring the final volume to 25 µl containing 1× Polymerase buffer (10 mM Tris-HCl, pH 7.0, 10 mM $MgCl_2$), 0.4 mM each dNTP, 2-5 Units Klenow Enzyme (Large Fragment DNA Polymerase I). The mixture was briefly centrifuged and incubated at 37° C. for 30 minutes. The reaction was stopped by heating at 65° C. for 15 min and placed on ice.

5. T7 In Vitro Transcription

One-half of the promoter synthesis reaction (12.5 µl) was heated at 37° C. for 10-15 min to re-anneal the T7 promoter-containing strands and then mixed with 12.5 µl of a Master Mixture solution to bring the final volume to 25 µl containing 1× Reaction buffer, 7.5 mM each rNTP, and 2 µl T7 RNA polymerase (MEGAscript™ Transcription Kit, Ambion). The mixture was briefly centrifuged and incubated in a thermocycler with a heated lid at 37° C. for 4-16 hrs. Alternatively, the mixture was incubated in a 37° C. heat block for 15 min, followed by incubation in an air hybridization oven at 37° for 4-16 hrs. It is essential to avoid evaporation and condensation of the reaction during this step.

6. sRNA Purification and Quantitation

The sRNA molecules were purified using the RNeasy Kit (Qiagen) following manufacturer's protocol for RNA cleanup. The purified sRNA molecules were eluted twice in 50 µl RNase-free water and quantified by UV-spectrophotometry in 0.1×TE Buffer, pH 8.0 at a wavelength ratio of 260/280.

Replicate amplifications were performed starting with 10 ng of total RNA or water alone (negative control). On average, 25 µg of amplified sRNA was recovered after amplifying 10 ng of total RNA vs. 0.5-4 µg of non-specific amplification product when using only water in the reverse transcription reaction in place of RNA representing 2500-fold amplification.

7. Reverse Transcription of sRNA

Twenty-five µl of sRNA was mixed with 1 µl sequence specific RT primer (500 ng/µl) (5'-CAA GCA GAA GAC GGC ATA CGA GAT CGG TCT CGG CAT CCT GCA CC GCT CTT CCG ATC TGA-3'; SEQ ID NO:4) (antisense RT primer $1^{st}$ strand) and heated at 80° C. for 10 min. The antisense RT primer contains a nucleotide sequence corresponding to the specific nucleotide sequence of the 5' extension of the first round RT primers (SeqA, nucleotides 49-60)—see accompanying figures) and contains additional sequence 5' to SeqA which is complementary to oligos on Illumina's Sequencer Flow Cell and Sequencing Primers (nucleotides 1-48). The reaction was immediately iced for 2 min, briefly centrifuged, and returned to ice. One µl dNTP mix (10 mM each) and 1 µl Superscript™ II reverse transcriptase (200 U/µl; Invitrogen) was added, and the RT reaction incubated at 42° C. for 1 hr. One µl RNase H (2 U/µl) (Invitrogen) was added, and the reaction incubated at 37° C. for 20 min. The reaction was then incubated at 65° C. to stop enzyme activity.

Second Strand Synthesis was performed by adding 1 µl sequence specific RT primer (500 ng/µl) (5'-AAT GAT ACG GCG ACC ACC GAG ATC TAC ACT CTT TCC CTA CAC GAC GCT CTT CCG ATC TTC-3'; SEQ ID NO: 5) (second strand sense primer) and heated at 80° C. for 10 min. The second strand sense primer contains a nucleotide sequence corresponding to SeqB, the specific nucleotide sequence of the sequence adjacent to the T7 promoter on the T7 Seq B promoter template (nucleotides 49-60, see accompanying figures), and contains additional sequence complementary to oligos on Illumina's Sequencer Flow Cell and Sequencing Primers (nucleotides 1-48). The reaction was immediately iced for 2 min, briefly centrifuged, and returned to ice. One µl dNTP mix (10 mM each) and 2 µl DNA Polymerase I (Invitrogen) was added, and the reaction incubated at 16° C. for 1 hr. The reaction was then incubated at 65° C. to stop enzyme activity. The reaction was purified using the MinElute™ PCR Purification Kit (Qiagen) according to the manufacturer's protocol and eluted in 10 µl EB Buffer provided by the manufacturer.

The double stranded cDNA produced is ready to be applied to Illumina's Genome Sequencer for analysis.

Example 2 sRNA Synthesis for Whole Transcriptome Sequencing

Method of FIG. 2A-C

1. First Strand cDNA Synthesis

For each RNA sample, the following RNA/primer mix was prepared on ice:

1. 1-8 μl total RNA (not exceeding 250 ng)
2. 2 μl first round oligodT sequence specific RT primer (50 ng/μl) (5'-CTT CCG ATC TGA TTT TTT TTT TT V-3', where V=C, G or A deoxyribonucleotides; SEQ ID NO:1), or
    1 μl first round random sequence specific RT primer (2× by mass of RNA) (5'-CTT CCG ATC TGA NNN NNN NNN-3, where N=A, G, C or T deoxyribonucleotides at random; SEQ ID NO:2)
3. RNase-free water to 11 μl The first round RT primers (first strand RT primers) comprise a 5' extension 12 nucleotides long which corresponds to a portion of the anchor sequence used by the Illumina sequencing system and which also generates a specific nucleotide sequence binding site for the antisense first strand RT primers (see accompanying figures). The RNA/primer mixture was heated at 80° C. for 10 minutes and immediately cooled on ice for 1-2 min. The mixture was then mixed with 9 μl of a Master Mixture solution to bring the final volume to 20 μl containing 1×RT buffer (50 mM Tris-HCl (pH 8.3), 75 mM KCl, 3 mM $MgCl_2$), 10 mM dithiothreitol (DTT), 0.5 mM each dNTP, 10 U Superase-In™ (Ambion), and 200 U Superscript™ II reverse transcriptase (Invitrogen). The mixture was briefly centrifuged and incubated at 42° C. for 2 hrs. Following a brief centrifugation, the reaction was adjusted to 100 μl with 1×TE (10 mM Tris-HCl, pH 8.0, 1 mM EDTA).

2. cDNA Purification

The reaction was purified using the RNeasy MinElute Kit (Qiagen) according to the manufacturer's protocol and eluted in 10 μl Nuclease-Free water provided by the manufacturer.

3. Tailing of First Strand cDNA

The first strand cDNA molecules were heated at 80° C. for 10 minutes and immediately cooled on ice for 1-2 min. The cDNA molecules in 10 μl were then mixed with 10 μl of a Master Mixture solution to bring the final volume to 20 μl containing 1× Tailing buffer (10 mM Tris-HCl, pH 7.0, 10 mM $MgCl_2$), 2.0 mM dATP, and 10 U terminal deoxynucleotidyl transferase (Roche Diagnostics). The mixture was briefly centrifuged and incubated at 37° C. for 2 min. The reaction was stopped by heating at 80° C. for 10 min and cooled at room temperature for 1-2 minutes.

4. T7 Promoter Synthesis

One μl of T7 RNA polymerase promoter template oligonucleotide (5'-TAA TAC GAC TCA CTA TAG GGA TTT TTT TTT TTT-3'; SEQ ID NO:6) (100 ng/μl) containing a 3' amino modifier was added to the oligodA-tailed cDNA molecules and the mixture incubated at 37° C. for 10 min to anneal the strands. The tailed cDNA molecules/bridge oligonucleotide/promoter template mixture was then mixed with 3 μl of a Master Mixture solution to bring the final volume to 25 μl containing 1× Polymerase buffer (10 mM Tris-HCl, pH 7.0, 10 mM $MgCl_2$), 0.4 mM each dNTP, 2-5 Units Klenow Enzyme (Large Fragment DNA Polymerase I). The mixture was briefly centrifuged and incubated at 37° C. for 30 minutes. The reaction was stopped by heating at 65° C. for 15 min and placed on ice.

5. T7 In Vitro Transcription

One-half of the promoter synthesis reaction (12.5 μl) was heated at 37° C. for 10-15 min to re-anneal the T7 promoter-containing strands and then mixed with 12.5 μl of a Master Mixture solution to bring the final volume to 25 μl containing 1× Reaction buffer, 7.5 mM each rNTP, and 2 μl T7 RNA polymerase (MEGAscript™ Transcription Kit, Ambion). The mixture was briefly centrifuged and incubated in a thermocycler with a heated lid at 37° C. for 4-16 hrs. Alternatively, the mixture was incubated in a 37° C. heat block for 15 min, followed by incubation in an air hybridization oven at 37° for 4-16 hrs. It is essential to avoid evaporation and condensation of the reaction during this step.

6. sRNA Purification and Quantitation

The sRNA molecules were purified using the RNeasy Kit (Qiagen) following manufacturer's protocol for RNA cleanup. The purified sRNA molecules were eluted twice in 50 μl RNase-free water and quantified by UV-spectrophotometry in 0.1×TE Buffer, pH 8.0 at a wavelength ratio of 260/280.

Replicate amplifications were performed starting with 10 ng of total RNA or water alone (negative control). On average, 25 μg of amplified sRNA was recovered after amplifying 10 ng of total RNA vs. 0.5-4 μg of non-specific amplification product when using only water in the reverse transcription reaction in place of RNA, representing 2500-fold amplification.

7. Reverse Transcription of sRNA

Twenty-five μl of sRNA was mixed with 1 μl sequence specific RT primer (500 ng/μl) (5'-CAA GCA GAA GAC GGC ATA CGA GAT CGG TCT CGG CAT TCC TGC ACC GCT CTT CCG ATC TGA-3'; SEQ ID NO:4) (antisense RT primer first strand) and heated at 80° C. for 10 min. The antisense RT primer contains a nucleotide sequence corresponding to the specific nucleotide sequence of the 5' extension of the first round RT primers (SeqA, nucleotides 49-60)—see accompanying figures) and contains additional sequence 5' to SeqA which is complementary to oligos on Illumina's Sequencer Flow Cell and Sequencing Primers (nucleotides 1-48). The reaction was immediately iced for 2 min, briefly centrifuged, and returned to ice. One μl dNTP mix (10 mM each) and 1 μl Superscript™ II reverse transcriptase (200 U/μl; Invitrogen) was added, and the RT reaction incubated at 42° C. for 1 hr. One μl RNase H (2 TRW) (Invitrogen) was added, and the reaction incubated at 37° C. for 20 min. The reaction was then incubated at 65° C. to stop enzyme activity.

Second Strand Synthesis was performed by adding 1 μl sequence specific RT primer (500 ng/μl) (5'-AAT GAT ACG GCG ACC ACC GAG ATC TAC ACT CTT TCC CTA CAC GAC GCT CTT CCG ATC TTC TTT TTT TTT VN-3'; SEQ ID NO:7) (second strand sense primer) and heated at 80° C. for 10 min. The second strand sense primer contains 5' nucleotide sequences corresponding to the specific nucleotide adapter sequences complementary to oligos on Illumina's Sequencer Flow Cell and Sequencing Primers (i.e., anchor sequences, sequencing primer recognition site and PCR primer recognition site, shown as SeqB in FIG. 2B) and 3' poly dT. The 3' end of the second strand sense primer may also terminated with VN as described above. The reaction was immediately iced for 2 min, briefly centrifuged, and returned to ice. One μl dNTP mix (10 mM each) and 2 μl DNA Polymerase I (Invitrogen) was added, and the reaction incubated at 16° C. for 1 hr. The reaction was then incubated at 65° C. to stop enzyme activity. The reaction was purified using the MinElute™ PCR Purification Kit (Qiagen) according to the manufacturer's protocol and eluted in 10 μl EB Buffer provided by the manufacturer.

The double stranded cDNA product is ready to be applied to Illumina's Genome Analyzer for analysis.

Based on published reference (Mamanova et al., *Nature Methods,* 7(2) 130-132 (2010)) the reverse transcription (double stranded cDNA synthesis) reaction may be performed on the flow cell prior to sequencing.

Note: Seq A and Seq B and associated 1st strand and 2nd strand double strand cDNA synthesis primers can be changed to any sequence as required by the particular sequencing platform to be combined with the described RNA amplification process. For example, a difference set of sequences will be required for the ABI SOLiD or Roche 454 Sequencer.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A method for producing double stranded cDNA from mRNA for use in a sequencing reaction comprising:
   a) reverse transcribing an isolated mRNA using a first primer hybridized thereto, the first primer comprising a random sequence or poly(dT) at a 3' end thereof and a first sequence required for a selected sequencing reaction at a 5' end thereof, thereby producing a first cDNA comprising the first sequence required for the selected sequencing reaction at a 5' end thereof;
   b) adding a first 3' homopolymeric tail to the first cDNA;
   c) hybridizing a single-stranded oligonucleotide to the 3' homopolymeric tail of the first strand cDNA, the single-stranded oligonucleotide comprising a 5' RNA polymerase promoter sequence and a second 3' homopolymeric tail which is complementary to the first 3' homopolymeric tail, thereby producing a partially double-stranded DNA with a 5' single-stranded overhang comprising the RNA polymerase promoter sequence;
   d) extending the 3' end of the cDNA, thereby producing a double stranded RNA polymerase promoter
   e) transcribing sRNA from the double-stranded RNA polymerase promoter, the sRNA comprising a complement of the first sequence required for the selected sequencing reaction at a 3' end thereof;
   f) reverse transcribing the sRNA using a second primer comprising the first sequence required for the selected sequencing reaction at a 3' end thereof, thereby producing a second cDNA comprising the first sequence required for the selected sequencing reaction at a 5' end thereof; and
   g) hybridizing to the second cDNA a third primer comprising a second sequence required for the selected sequencing reaction at a 3' end thereof and extending the third primer, thereby producing the double-stranded cDNA for use in the sequencing reaction.

2. The method of claim 1 wherein the single-stranded oligonucleotide further comprises the second sequence required for the selected sequencing reaction between the RNA polymerase promoter and the 3' poly(dT) tail.

3. The method of claim 2 wherein the second primer further comprises at least a third sequence required for the selected sequencing reaction at a 5' end thereof.

4. The method of claim 3 wherein the third primer further comprises at least a fourth sequence required for the selected sequencing reaction at a 5' end thereof.

5. The method of claim 4 wherein the at least a third sequence and the at least a fourth sequence are independently selected from the group consisting of a sequence for hybridization of a sequencing primer and a sequence for hybridization of an amplification primer.

6. The method of claim 1 wherein steps (e)-(g) are performed on a flow cell for DNA sequencing.

7. The method of claim 1 wherein the RNA polymerase promoter is selected from the group consisting of T7 promoters, T3 promoters and SP6 promoters.

8. The method of claim 1 wherein the single-stranded oligonucleotide comprises SEQ ID NO:3, second primer comprises SEQ ID NO:4 and the third primer comprises SEQ ID NO:5.

9. The method of claim 1 wherein the single-stranded oligonucleotide comprises SEQ ID NO:6, the second primer comprises SEQ ID NO:4 and the third primer comprises SEQ ID NO:7.

10. The method of claim 1 wherein the single-stranded oligonucleotide comprises DNA polymerase blocker at a 3' terminus thereof.

11. The method of claim 10 wherein the DNA polymerase blocker is selected from the group consisting of 3' amino modifiers, 3' deoxyterminators and 3' dideoxyterminators.

12. The method of claim 1 wherein the first 3' homopolymeric tail is poly(dA) and the second 3' homopolymeric tail is poly(dT) or the first 3' homopolymeric tail is poly(dT) and the second 3' homopolymeric tail is poly(dA).

13. The method of claim 1 wherein
   a. the first primer is poly(dT) and terminates with TV-3', and/or
   b. the single-stranded oligonucleotide terminates with TV-3', wherein V is any base except T or U.

14. The method of claim 1 wherein the third primer comprises a homopolymeric segment complementary to a homopolymeric sequence at a 3' end of the second cDNA.

15. The method of claim 14 wherein the third primer terminates with TV-3', wherein V is any base except T or U.

16. The method of claim 1 further comprising sequencing the double-stranded cDNA using a sequencing primer comprising a 3' homopolymeric tail complementary to a homopolymeric segment of the cDNA derived from the first primer and/or the single-stranded oligonucleotide.

17. The method of claim 16 wherein the complementary homopolymeric tail of the sequencing primer is similar in length to the homopolymeric segment in the cDNA.

18. The method of claim 1 further comprising sequencing a homopolymeric segment of the double-stranded cDNA derived from the first primer and/or the single-stranded oligonucleotide using non-fluorescent nucleotides.

19. A method for producing double stranded DNA for use in a sequencing reaction comprising:
   a) reverse transcribing an isolated mRNA using a first primer hybridized thereto, the first primer comprising a random sequence or poly(dT) at a 3' end thereof and a first sequence required for a selected sequencing reaction at a 5' end thereof, thereby producing a first cDNA comprising the first sequence required for the selected sequencing reaction at a 5' end thereof;
   b) adding a 3' poly(dT) or a 3' poly(dA) homopolymeric tail to the first cDNA
   c) hybridizing a single-stranded oligonucleotide to the 3' homopolymeric tail of the first strand cDNA, the single-stranded oligonucleotide comprising a 5' RNA polymerase promoter sequence, a 3' sequence complementary to the 3' homopolymeric tail, a sequence corresponding to a second sequence required for the selected sequencing reaction between the RNA polymerase promoter sequence and the 3' sequence complementary to the 3' homopolymeric tail, and a DNA polymerase blocker at the 3' terminus, thereby producing a partially double-stranded DNA with a 5' single-stranded overhang comprising the RNA polymerase promoter sequence;
   d) extending the 3' end of the cDNA, thereby producing a double stranded RNA polymerase promoter
   e) transcribing sRNA from the double-stranded RNA polymerase promoter, the sRNA comprising the second sequence required for the selected sequencing reaction at a 5' end thereof and a complement of the first sequence required for the selected sequencing reaction at a 3' end thereof;
   f) reverse transcribing the sRNA using a second primer comprising the first sequence required for the selected sequencing reaction at a 3' end thereof and at least a third sequence required for the selected sequencing reaction at a 5' end thereof, thereby producing a second cDNA comprising the first sequence required for the selected sequencing reaction at a 5' end thereof; and
   g) hybridizing to the second cDNA a third primer comprising the second sequence required for the selected sequencing reaction at a 3' end thereof and at least a fourth sequence required for the selected sequencing system or reaction at a 5' end thereof and extending the third primer, thereby producing the double-stranded cDNA for use in the sequencing reaction.

\* \* \* \* \*

```
                        SEQUENCE LISTING

<160> NUMBER OF SEQ ID NOS: 7

<210> SEQ ID NO 1
<211> LENGTH: 24
<212> TYPE: DNA
<213> ORGANISM: Artificial Sequence
<220> FEATURE:
<223> OTHER INFORMATION: Primer

<400> SEQUENCE: 1
cttccgatct gattttttttt tttv                                            24

<210> SEQ ID NO 2
<211> LENGTH: 21
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (13)..(21)
<223> OTHER INFORMATION: n is a, c, g, or t

<400> SEQUENCE: 2
cttccgatct gannnnnnnn n                                                21

<210> SEQ ID NO 3
<211> LENGTH: 44
<212> TYPE: DNA
<213> ORGANISM: Artificial Sequence
<220> FEATURE:
<223> OTHER INFORMATION: Transcription promoter oligo
<220> FEATURE:
<221> NAME/KEY: promoter
<222> LOCATION: (1)..(21)
<220> FEATURE:
<221> NAME/KEY: misc_structure
<222> LOCATION: (44)..(44)
<223> OTHER INFORMATION: 3' amino modifier

<400> SEQUENCE: 3
taatacgact cactataggg acttccgatc tctttttttt tttt                       44

<210> SEQ ID NO 4
<211> LENGTH: 60
<212> TYPE: DNA
<213> ORGANISM: Artificial Sequence
<220> FEATURE:
<223> OTHER INFORMATION: Primer

<400> SEQUENCE: 4
```

```
caagcagaag acggcatacg agatcggtct cggcattcct gcaccgctct tccgatctga    60

<210> SEQ ID NO 5
<211> LENGTH: 60
<212> TYPE: DNA
<213> ORGANISM: Artificial Sequence
<220> FEATURE:
<223> OTHER INFORMATION: Primer

<400> SEQUENCE: 5
aatgatacgg cgaccaccga gatctacact ctttccctac acgacgctct tccgatcttc    60

<210> SEQ ID NO 6
<211> LENGTH: 33
<212> TYPE: DNA
<213> ORGANISM: Artificial Sequence
<220> FEATURE:
<223> OTHER INFORMATION: Transcription promoter oligo
<220> FEATURE:
<221> NAME/KEY: promoter
<222> LOCATION: (1)..(21)
<220> FEATURE:
<221> NAME/KEY: misc_structure
<222> LOCATION: (33)..(33)
<223> OTHER INFORMATION: 3' amino modifier

<400> SEQUENCE: 6
taatacgact cactataggg attttttttt ttt                                  33

<210> SEQ ID NO 7
<211> LENGTH: 73
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (73)..(73)
<223> OTHER INFORMATION: n is a, c, g, or t

<400> SEQUENCE: 7
aatgatacgg cgaccaccga gatctacact ctttccctac acgacgctct tccgatcttc    60
tttttttttt tvn                                                        73
```